(12) United States Patent
Murphy

(10) Patent No.: US 9,119,631 B1
(45) Date of Patent: *Sep. 1, 2015

(54) DUAL-BLADED SURGICAL SAW AND METHODS OF USE

(71) Applicant: Christopher B. Murphy, Edgewater, FL (US)

(72) Inventor: Christopher B. Murphy, Edgewater, FL (US)

( * ) Notice: Subject to any disclaimer, the term of this patent is extended or adjusted under 35 U.S.C. 154(b) by 148 days.

This patent is subject to a terminal disclaimer.

(21) Appl. No.: 13/826,850

(22) Filed: Mar. 14, 2013

Related U.S. Application Data

(63) Continuation of application No. 13/597,851, filed on Aug. 29, 2012, now Pat. No. 8,888,784.

(51) Int. Cl.
  *A61B 17/14* (2006.01)
  *B26B 3/04* (2006.01)
  *A61B 17/16* (2006.01)

(52) U.S. Cl.
  CPC ........... *A61B 17/148* (2013.01); *A61B 17/1682* (2013.01); *B26B 3/04* (2013.01)

(58) Field of Classification Search
  CPC ..... A61B 17/148; A61B 17/1682; B26B 3/04
  USPC ................ 606/79, 82, 171; 30/369, 208, 266, 30/279.2, 299, 303, 302, 304; 173/214
  See application file for complete search history.

(56) References Cited

U.S. PATENT DOCUMENTS

| H0000571 H | 2/1989 | Hollinger et al. |
|---|---|---|
| 5,470,335 A | 11/1995 | Du Toit |
| 6,007,541 A | 12/1999 | Scott |
| 6,860,886 B1 | 3/2005 | Lee |
| 7,744,616 B2 | 6/2010 | O'Donoghue |
| 2004/0243136 A1 | 12/2004 | Gupta et al. |
| 2011/0230887 A1 | 9/2011 | Bickenbach |

OTHER PUBLICATIONS

U.S. Statutory Invention Registration H571 for Double-Bladed, Water-Cooled Attachment for Surgical Bone Cutting Saw and Method for Using and Assembling the Same, Hollinger et. al, Feb. 7, 1989.
MicroAire Series 7000 Oscillating Saw, Battery Electric (2 pages) www.microaire.com.
MicroAire Oscillating Saw, Pneumatic Hall Connector (2 pages) www.microaire.com.
MicroAire Large Power Oscillating Saw Blades (1 page) www.microaire.com.

*Primary Examiner* — Andrew Yang
(74) *Attorney, Agent, or Firm* — Allen Dyer Doppelt Milbrath & Gilchrist

(57) ABSTRACT

A dual-bladed surgical saw and methods of use are described. A preferred embodiment of the dual-bladed surgical saw include a saw body having a blade assembly attached thereto, the blade assembly being positioned about a rotational axis. A first blade is radially spaced about the rotational axis, extending outwardly from the blade assembly substantially parallel to the rotational axis, and terminating at a first cutting surface. A second blade is radially spaced about the rotational axis, extending outwardly from the blade assembly parallel to the rotational axis, and terminating at a second cutting surface. An oscillator mechanism is coupled to the first and second blades for simultaneously reciprocating the first and second blades. The first blade is independently rotatable relative to the second blade about the rotational axis for defining a predetermined cutting angle between the first blade and second blade.

20 Claims, 16 Drawing Sheets

Sect. IV - IV

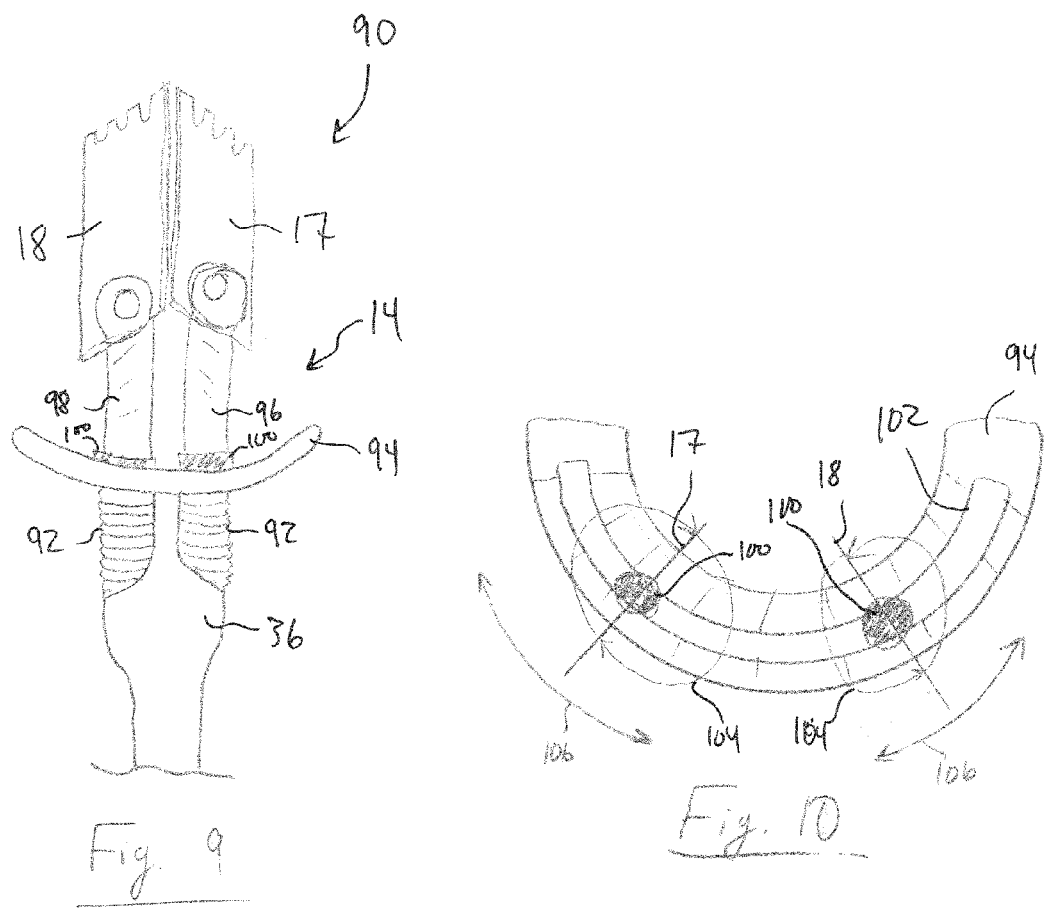

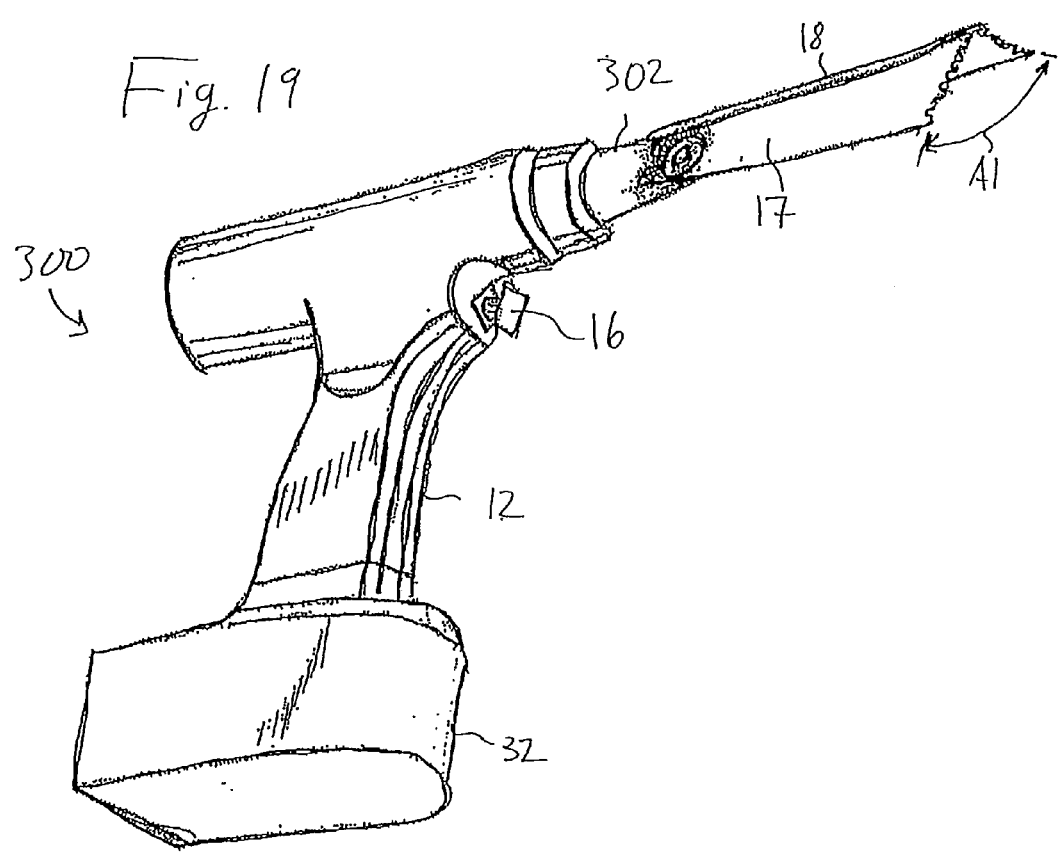

DUAL-BLADED SURGICAL SAW AND METHODS OF USE

This is a continuation-in-part of application Ser. No. 13/597,851, filed Aug. 29, 2012 and titled "Dual Bladed Surgical Saw and Methods of Use," which is incorporated by reference herein in its entirety.

FIELD OF THE INVENTION

The invention relates to the field of surgical saws and, more particularly, to dual-bladed surgical saws for shaping bone.

BACKGROUND

Certain surgical procedures require bones to be cut at precise angles. For example, the Austin, or Chevron, bunionectomy requires the medical professional to make a precise sixty degree angled cut into the first metatarsal head so that the two resulting metatarsal sections can be translated sideways and affixed together. Likewise, in knee replacement surgery, the lower end of the femur must be cut to match the shape of the particular knee replacement implant that will be used.

In a typical knee replacement procedure, the femur is shaped by making a series of cuts with a single-bladed surgical saw. A cutting guide is used to help the surgeon make the appropriately angled cuts. The cutting guide is pinned in place on the femur and the saw is used to make the first cut. The cutting guide is then repositioned on the femur and the saw is used to make the second cut. These repositioning and cutting steps are performed sequentially until all of the necessary cuts are complete.

Although the conventional knee replacement procedure works well, it is inefficient and more complicated than it needs to be.

SUMMARY

The various aspects of the invention solve this problem by providing a dual-bladed surgical saw, including a pair of blades that can be set at a desired angle relative to one another for simultaneously making a pair of cuts that are angled relative to one another at the desired angle.

In a preferred embodiment, the dual-bladed surgical saw includes a saw body having a blade assembly attached thereto, the blade assembly being positioned about a rotational axis. A first blade is radially spaced about the rotational axis, extending outwardly from the blade assembly substantially parallel to the rotational axis, and terminating at a first cutting surface. A second blade is radially spaced about the rotational axis, extending outwardly from the blade assembly parallel to the rotational axis, and terminating at a second cutting surface. An oscillator mechanism is coupled to the first and second blades for simultaneously reciprocating the first and second blades. The first blade is independently rotatable relative to the second blade about the rotational axis for defining a predetermined cutting angle between the first blade and second blade.

In another preferred embodiment, a dual-bladed surgical saw includes a saw body having a first blade assembly and a second blade assembly attached thereto. The first blade assembly includes a first oscillator for reciprocating a first blade having a cutting surface at an end of the first blade opposite the first oscillator. The second blade assembly includes a second oscillator for reciprocating a second blade having a cutting surface at an end of the second blade opposite the second oscillator. The first blade is independently rotatable relative to the second blade about a rotational axis passing through the first and second blade assemblies for defining a predetermined cutting angle between the first blade and second blade.

In a method aspect of the invention, a method of shaping bone for mating the bone with an implant having an implant surface adapted to abut the shaped bone when installed involves positioning the blades of a dual-bladed surgical saw to a predetermined cutting angle and simultaneously making first and second adjacent cuts separated by the cutting angle by contacting the bone with the first and second blades. A third cut adjacent to the second cut and separated from the second cut by the same or a different cutting angle is formed in the bone by passing the first blade across the second cut while the second blade makes the third cut.

These aspects of the invention, along with other additional aspects, embodiments, and features will be better understood by referring to the accompanying drawings and the Detailed Description of Preferred Embodiments.

BRIEF DESCRIPTION OF THE DRAWINGS

FIG. 9 is a top plan view of an alternate form of the cutting head, according to a fifth apparatus aspect of the invention;

FIG. 10 is a partial front view of the cutting head shown in FIG. 9;

FIG. 19 is a right side perspective view of a sagittal-type dual-bladed surgical saw with a fixed cutting angle, according to a seventh apparatus aspect of the invention.

DETAILED DESCRIPTION OF PREFERRED EMBODIMENTS

In the Summary above and in the Detailed Description of Preferred Embodiments, reference is made to particular features (including method steps) of the invention. Where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other ingredients, features, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

In this section, the invention will be described more fully with reference to certain preferred embodiments. This invention may, however, be embodied in many different forms and should not be construed as limited to the embodiments set forth herein. Rather, these embodiments are provided so that this disclosure will convey preferred embodiments of the invention to those skilled in the art.

Figure 1:
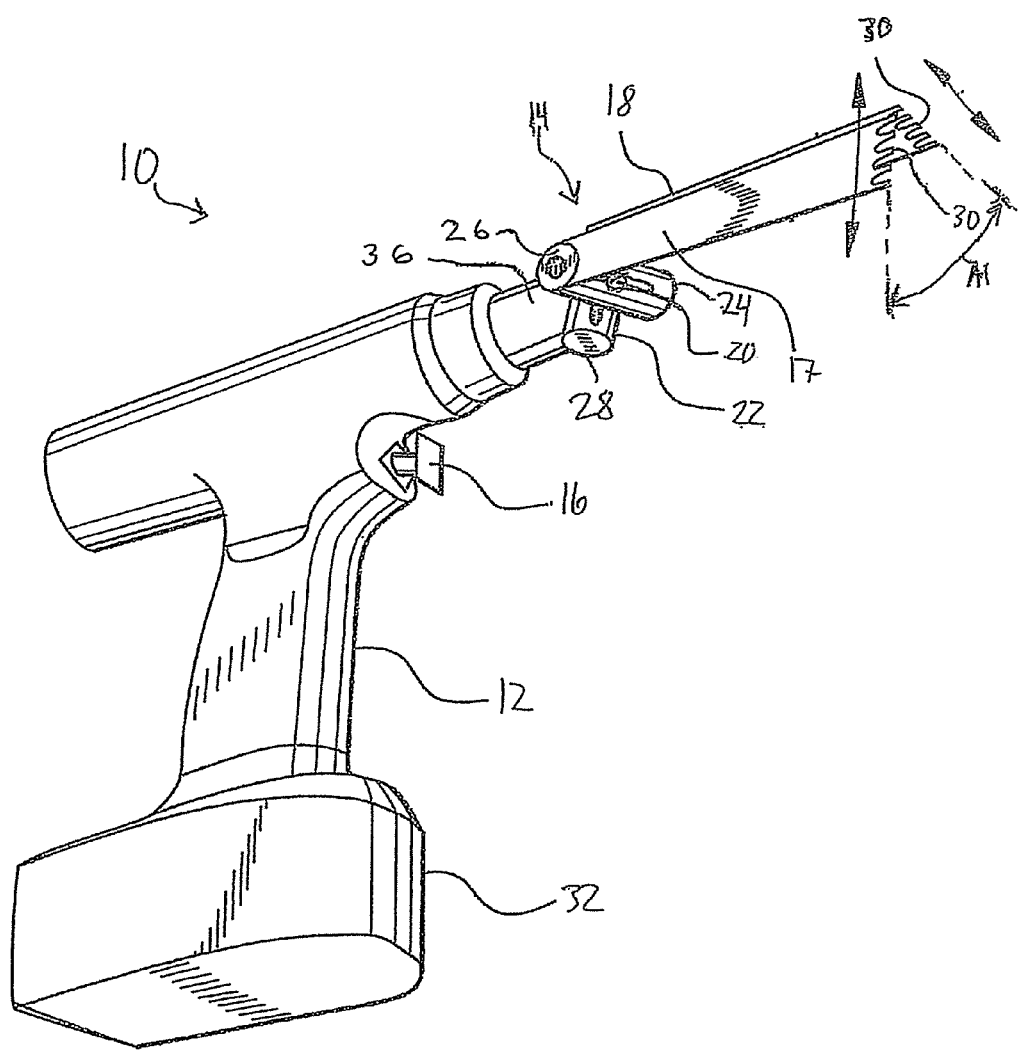
FIG. 1 is a right side perspective view of a dual-bladed surgical saw, according to a first apparatus aspect of the invention.
Figure 2:
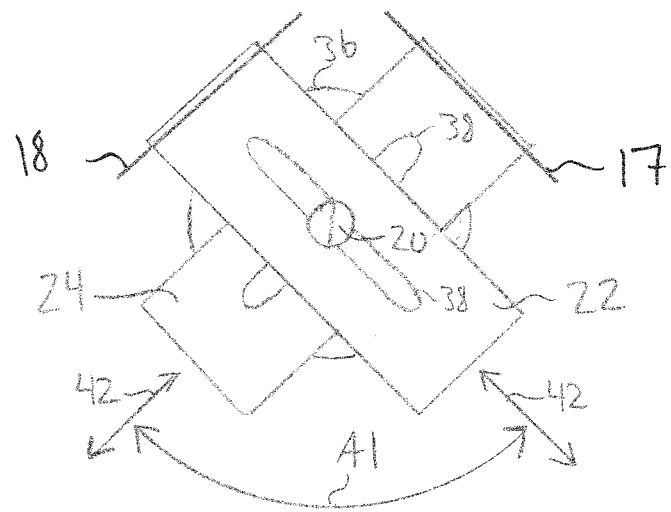
FIG. 2 is a front elevation view of the blade assembly of the dual-bladed surgical saw of FIG. 1.

Referring initially to FIGS. 1 and 2 a dual-bladed surgical saw 10, according to a first apparatus aspect of the invention includes a saw body 12, a cutting head 14, and a switch 16 for turning the motion of a pair of saw blades 16, 18 on and off. An angle A1 between the saw blades 16, 18 is adjustable by manipulating an adjustment pin 20.

The cutting head 14 includes a first blade assembly 22 and a second blade assembly 24. The first blade assembly 22 includes the first blade 17, whereas the second blade assembly 24 includes the second blade 18. Each blade 17, 18 is attached to an oscillator 26, 28 at one end and includes a cutting surface 30 at the opposite end. In the preferred embodiment shown, the cutting surface is in the form of saw teeth, but any other conventional cutting surface may be used.

The body 12 houses electrical components used to operate the saw 10 via the switch 16. In this particular embodiment, a battery 32 provides power to the cutting head 14 to oscillate the blades 17, 18. When the switch 16 is in the on position, the first and second oscillators 26, 28 oscillate, causing the first and second blades 17, 18 to reciprocate as indicated by the arrows. Other types of power sources such as other electric or even pneumatic power sources can be used to drive the oscillators 26, 28 without departing from the scope of the invention.

The first and second blades 17,18 are positioned at an angle A1 relative to one another. The angle may be predetermined depending on the type of surgery to be performed and is adjustable so that multiple angled cuts can be made using the same saw in the same surgical procedure.

Figure 3:
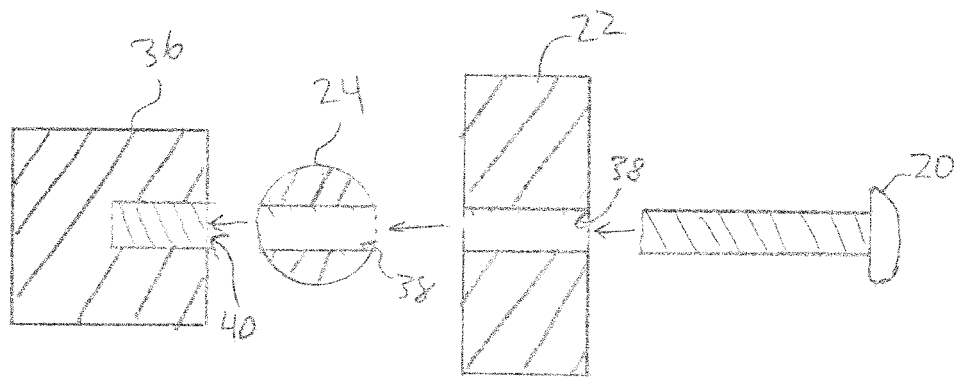
FIG. 3 is an exploded side cross-sectional view of the blade assembly of FIG. 3.

As best shown in FIGS. 2 and 3, the adjustment pin 20 is adapted to allow the angle between the blades 17,18 to be adjusted by loosening and tightening the first and second blade assemblies 22, 24 against a blade assembly mounting member 36. In the embodiment shown, the adjustment pin 20 is a threaded fastener, which passes through an elongated slot 38 formed through the first blade assembly 22 and second blade assembly 24 and fits into a threaded bore 40 in the blade assembly mounting member 36. By loosening the adjustment pin 20, the force holding the pieces together is reduced, allowing the first and second blade assemblies 22,24 to be rotated to the desired angle A1. If desired, the radial distance between each blade 17,18 can be increased or decreased by sliding the respective blade assembly 22,24 along its respective slot 38 in the direction shown by the arrows 42.

Figure 4A:
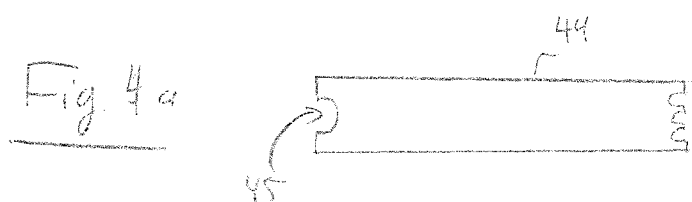
FIGS. 4a-c are right side elevation views of various saw blade shapes that may be used with the dual-bladed surgical saw.
Figure 4B:
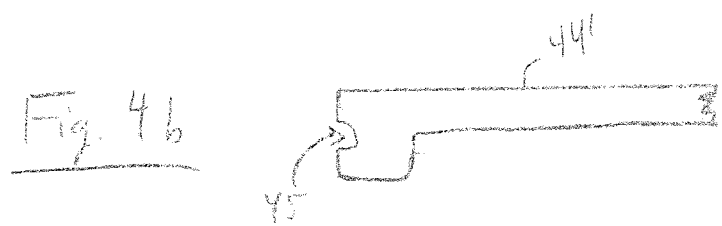
Figure 4C:
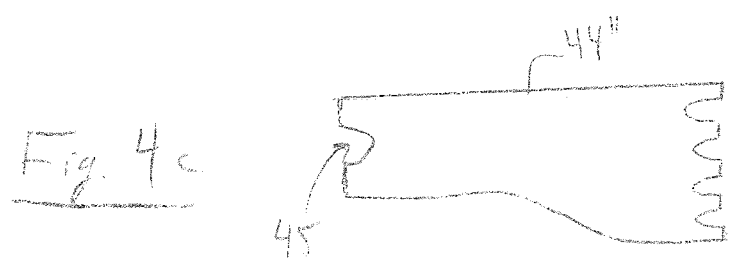

Referring to FIGS. 4a-c, the different shaped blades 44, 44', 44" can be mounted on the blade assembly 22,24 to provide additional adaptability to various surgical procedures. The blades 44,44',44" include an indented attachment member 45 for attachment to the saw 10. The blades 44, 44', 44" can have varying widths so that the saw 10 can be adapted to different sizes of bone or different osteotomies.

Figure 5:
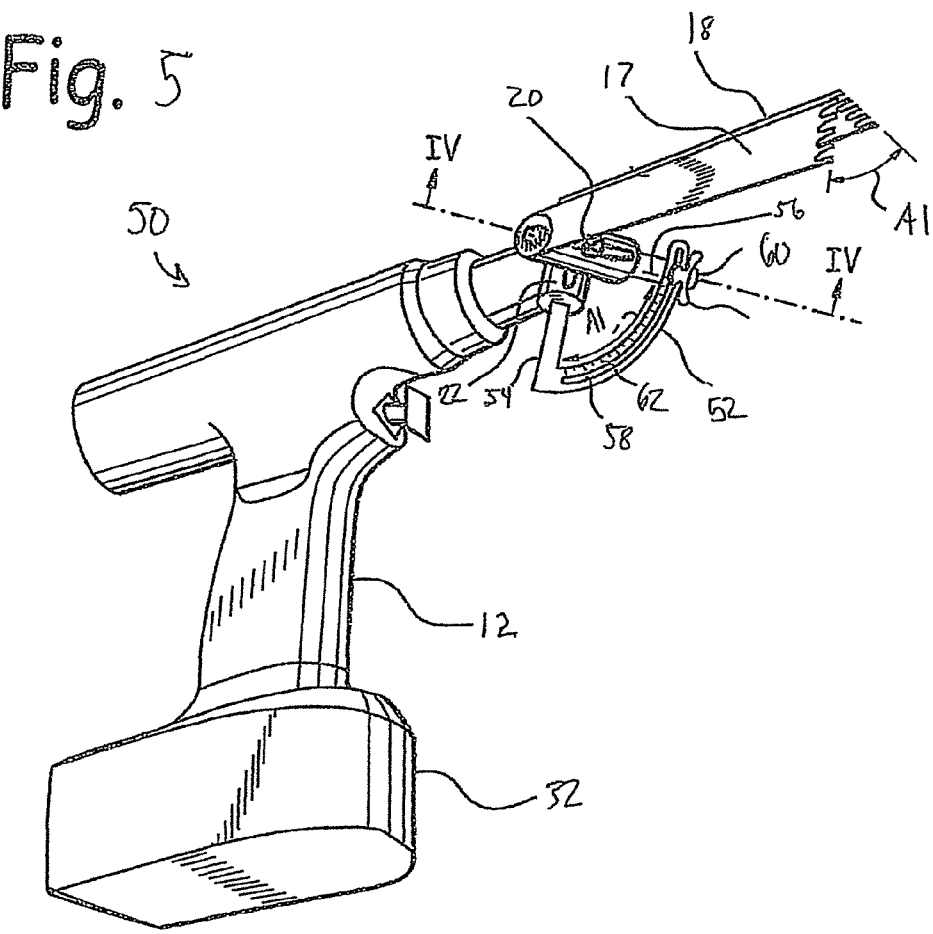
FIG. 5 is a right side perspective view of a dual-bladed surgical saw, according to a second apparatus aspect of the invention.
Figure 6:
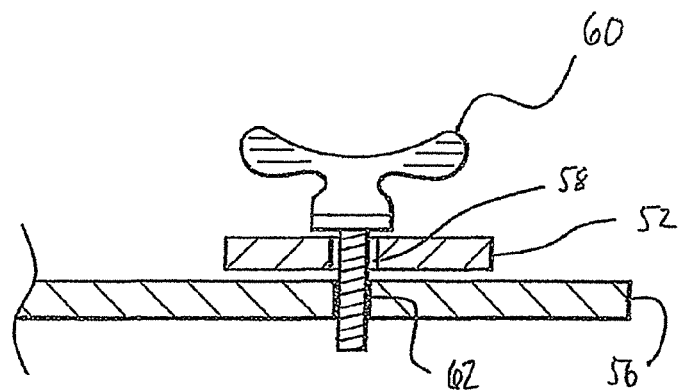
FIG. 6 is a side cross-sectional view of a fastener, goniometer, and second blade assembly arm taken at section IV-IV of FIG. 5.

Referring to FIGS. 5 and 6, a dual-bladed surgical saw 50, according to a second apparatus aspect of the invention, includes a goniometer 52 for setting the blade angle A1 between the first and second blades 17, 18. In this embodiment, the first blade assembly 22 includes a first blade assembly arm 54 attached to and extending therefrom. The second blade assembly includes a second blade assembly arm 56 attached to and extending therefrom. The goniometer 52 is arcuate shaped and is attached at one end to the first blade assembly arm 54 and at the other end to the second blade assembly arm 56. A goniometer slot 58 is formed through the goniometer 52 for allowing a goniometer fastener 60 to slide therethrough as the angle A1 is adjusted. Angular markings 62 are positioned along the goniometer slot 58 to indicate the angle A1.

As best shown in FIG. 6, the goniometer fastener 60 includes a threaded end the feeds through a threaded bore 62 in the second blade assembly 24 for releasably fix the position of the goniometer 52. The goniometer fastener 60 slides through the goniometer slot 58 as shown. The angle A1 is defined by the position of the goniometer fastener 60 along the goniometer slot 58 as indicated by the angular markings 62.

In use, the goniometer fastener 60 is inserted through the goniometer slot 58 and threaded loosely into the threaded bore 62 in the second blade assembly arm 56. The blade angle A1 is set as desired by rotating the second blade assembly arm 56 until the desired angle A1 is obtained. The goniometer fastener is then tightened into the threaded bore 60, pressing the goniometer 52 between the second blade assembly arm 56 and the head of the goniometer fastener 60 to fix the blade angle A1 in position.

Figure 7:
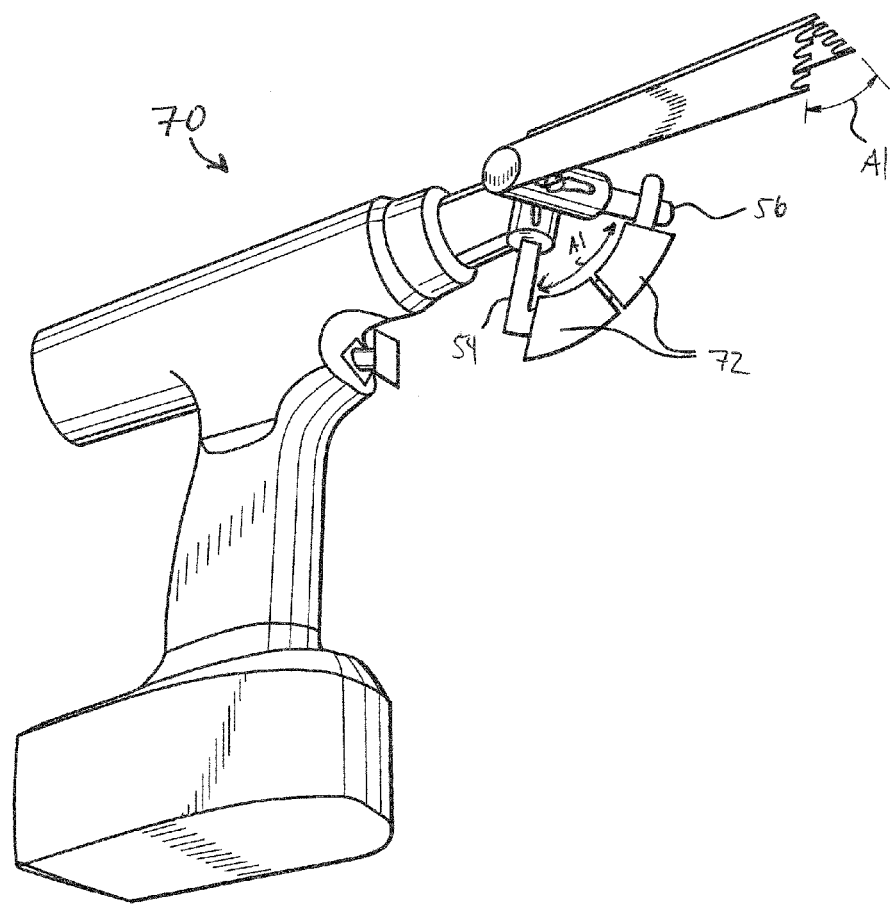
FIG. 7 is a right side perspective view of a dual-bladed surgical saw, according to a third apparatus aspect of the invention.

Referring to FIG. 7, a dual-bladed surgical saw 70, according to a third apparatus aspect of the invention, includes a pair of shims 72 that are used to set the blade angle A1. The shims 72 are inserted between the first and second blade assembly arms 54,56 as appropriate for obtaining the desired blade angle A1. The use of shims 72 is especially useful where a pre-determined blade angle A1, such as sixty degrees is desired. The blade angle can quickly be obtained by inserting the appropriately sized shims 72.

Figure 8:
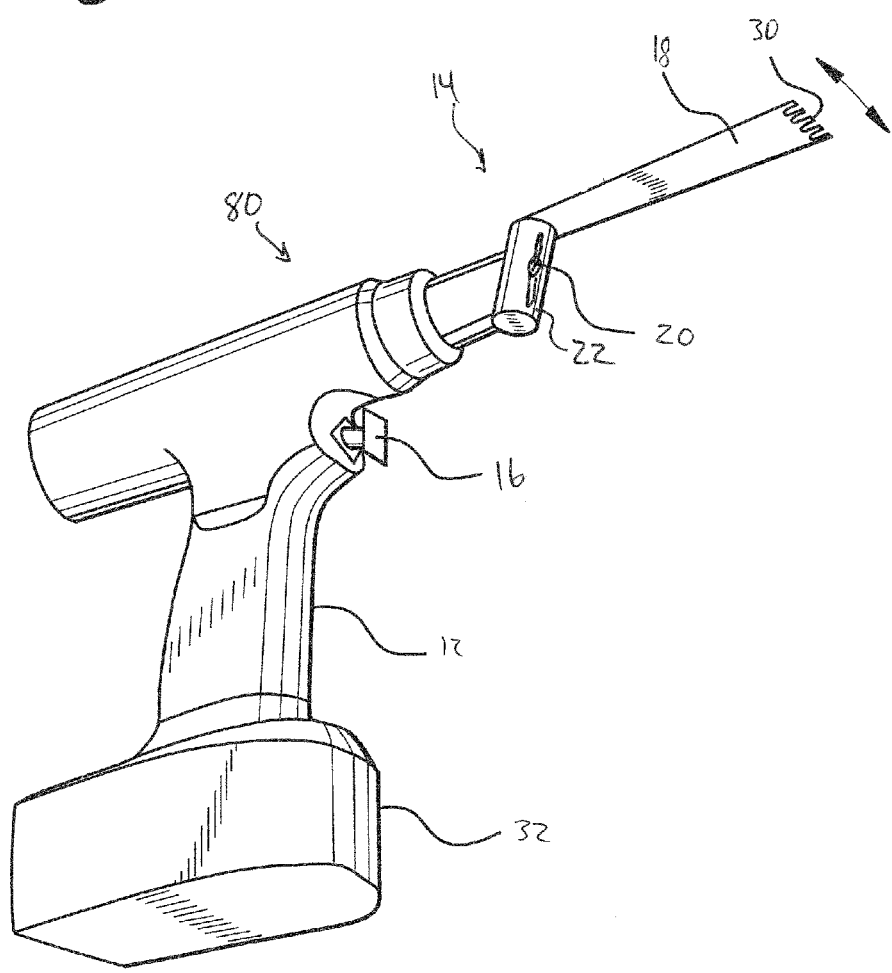
FIG. 8 is a right side perspective view of a dual-bladed surgical saw, according to a fourth apparatus aspect of the invention, with one of the blades removed.

Referring to FIG. 8, a modified dual-bladed surgical saw 80, according to a fourth apparatus aspect of the invention, is modified by having the first blade assembly (not shown removed so that the cutting head 14 only includes the second blade assembly 22 with the second blade 18 attached thereto. In this embodiment, the saw 80 may be used as a conventional, single bladed surgical saw.

Referring to FIGS. 9 and 10, a dual-bladed surgical saw 90, according to a fifth apparatus aspect of the invention, includes a different type of cutting head 14. In this embodiment, the mounting member 36 has a pair of flexible arms 92 extending outwardly therefrom to a goniometer 94. The blades 17, 18 are mounted about blade mounts 96,98 at a distal end relative to the flexible arms 92. A pair of blade mount fasteners 100 fasten the blade mounts 96,98 to the flexible arms 92. The fasteners 100 pass through a goniometer slot 102.

In this embodiment, the blades 17, 18 can be rotated 360 degrees about an axis passing through the respective fastener 100 as illustrated by the arrows 104. The blades 17, may also be positioned along the slots 102 to the desired blade angle as illustrated by arrows 106. The flexible arms 92 flex as the blade angle is changed.

It should be noted that the apparatus aspects of the invention described above are directed to surgical saws of the sagittal type, but the scope of the invention is not limited only to this type.

Figure 11:
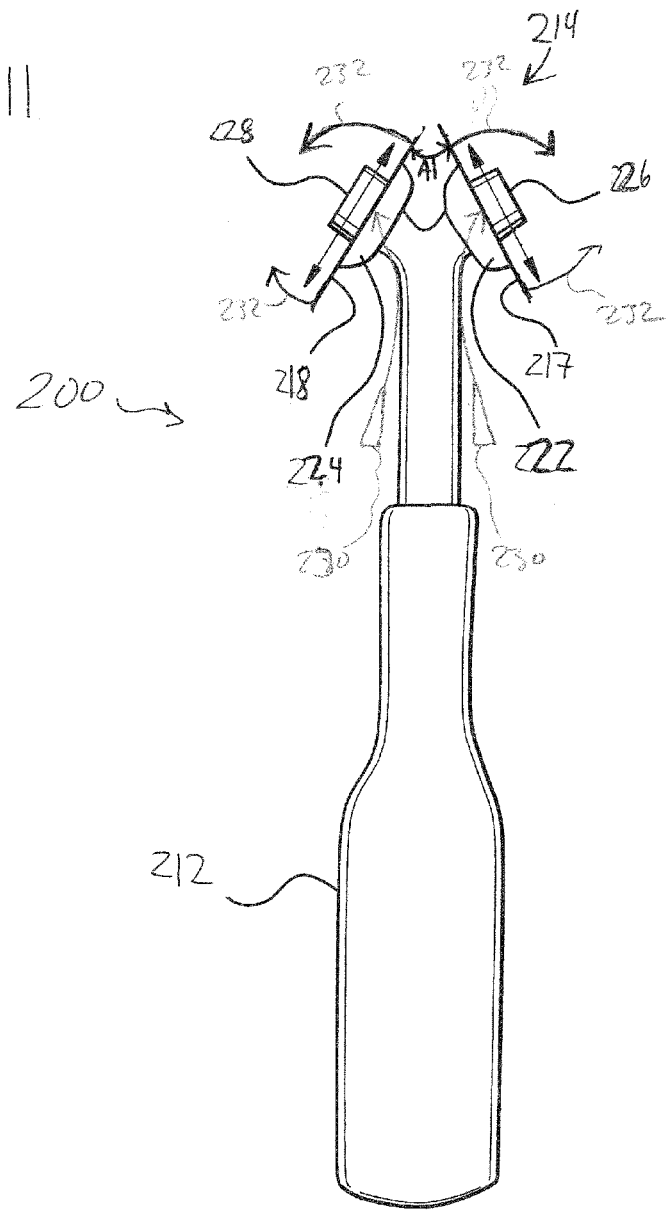
FIG. 11 is a rear isometric view of a dual-bladed surgical saw, according to a sixth apparatus aspect of the invention.

Referring to FIG. 11, an oscillating type surgical saw, according to a sixth apparatus aspect of the invention includes a saw body 212, an oscillating saw-type cutting head 214, a first blade 217 and a second blade 218. The blades 217, 218 are coupled, respectively, to first and second blade assemblies 222, 224. A pair of oscillators 226, 228 reciprocate the blades 217, 218 when activated. In this embodiment the cutting angle A1 between the blades 217, 218 is fixed, but can be adjusted by inserting one or more angled shim blocks 230 between the blades 217, 218 and the blade assemblies 224, 226. The cutting angle A1 is then determined from the angle forming the angled shim blocks 230. This allows the blades 217,218 to be adjusted in the direction indicated by the arrows 232. In an alternate example, the cutting angle A1 is adjusted by changing the blade width, which may also be done in combination with using one or more shim blocks 230.

Figure 12:
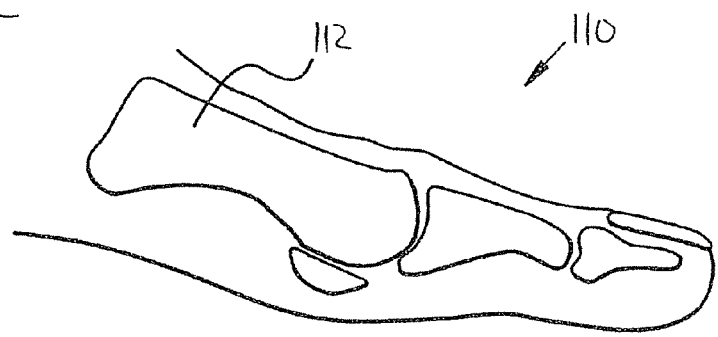
FIGS. 12-14 illustrate a method of use for a dual-bladed surgical saw, according to a first method aspect of the invention.
Figure 13:
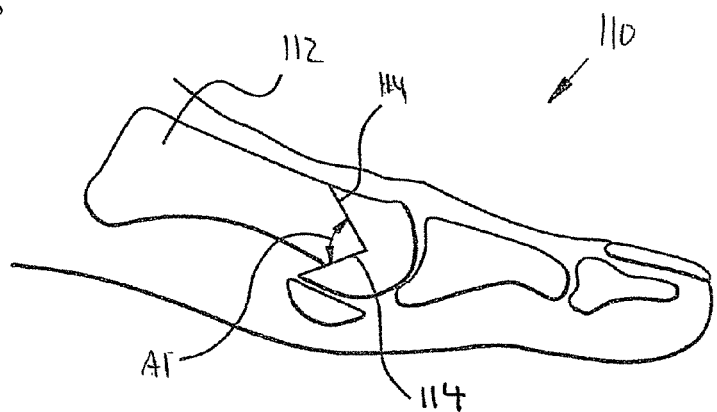
Figure 14:
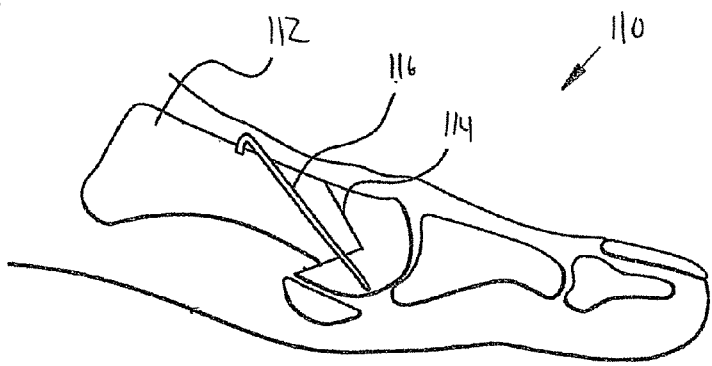

FIGS. 12-14 illustrate a first method of use aspect of the invention, in which a dual-bladed surgical saw according to one of the apparatus aspects of the invention is used to perform an Austin bunionectomy on a foot 110. In this method, the blade angle is set to the desired position and the dual-bladed surgical saw is started. A cut 114 is made in the first metatarsal 112 at the blade angle A1. The first metatarsal 112 is then fixed in place using an appropriate fixation device 116 such as a K-wire. The procedure is then concluded in the conventional manner.

Figure 15:
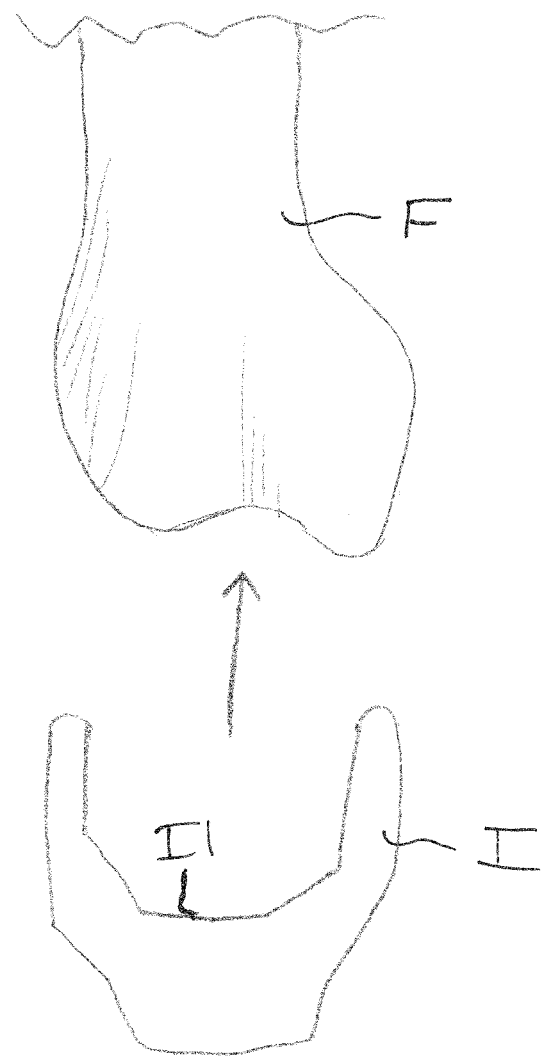
FIG. 15 is a schematic illustration of a lower portion of a femur and a knee replacement implant that is to be affixed thereto.

Referring now to FIG. 15, one of the particularly advantageous methods of use of the dual-bladed surgical saws described above is to shape a femur F so that a knee implant I can be installed. Knee implants typically include an implant surface I1 that is placed in contact with the shaped femur F and affixed thereto. The implant surface I1 has a very particular shape, including differently angled sections. In order for the knee replacement procedure to be effective, the shape of the femur F should substantially match the shape of the implant surface I1. Conventionally, the femur F is shaped using a single bladed surgical saw, which has the drawbacks discussed above.

Figure 16A:
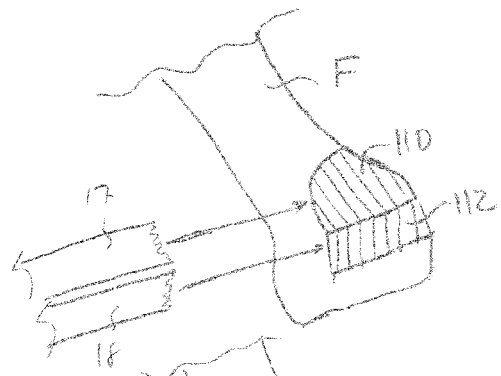
FIGS. 16a-d illustrate a method of use for a dual-bladed surgical saw, according to a second method aspect of the invention.
Figure 16B:
Figure 16C:
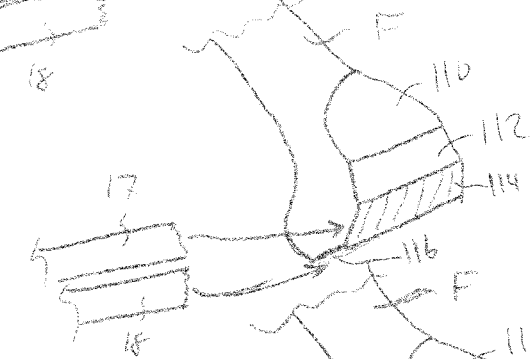
Figure 16D:
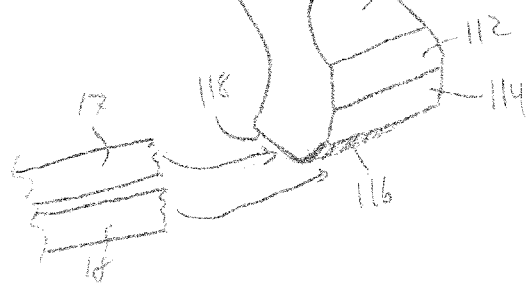
Figure 17:
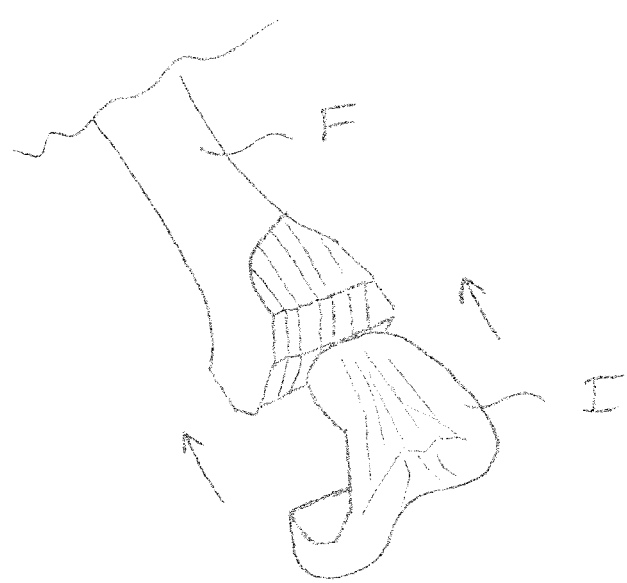
FIG. 17 illustrates the implant being placed onto the shaped femur.

Knee replacement surgery is made more efficient by utilizing a dual-bladed surgical saw because it can make a precisely angled cut in the femur F in one pass. This is illustrated in FIGS. 16a-d. In FIG. 16a, the blades 17,18 are positioned at the desired angle and a first pass is made across the femur F to form a first and second cut 110, 112 separated by the blade angle. In FIG. 16b, the blades 17,18 are repositioned, if necessary, to the desired angle and a second pass is made across the femur F to form a third cut 114 separated from the second cut 112 by the blade angle. Note that in the second pass, the first blade 17 runs back across the second cut 112 to ensure that the third cut 114 is as close as possible to the correct angle. In FIG. 16c, the blades 17,18 are repositioned, if necessary, to the desired angle and a third pass is made across the femur F to form a fourth cut 116 separated from the third cut 114 by the blade angle. In the third pass, the first blade 17 runs back across the third cut 114 to ensure that the fourth cut 116 is as close as possible to the correct angle. In FIG. 16d, the blades 17,18 are repositioned, if necessary, to the desired angle and a fourth pass is made across the femur F to form a fifth cut 118 separated from the fourth cut 116 by the blade angle. In the fourth pass, the first blade 17 runs back across the fourth cut 116 to ensure that the fifth cut 118 is as close as possible to the correct angle. FIG. 17 illustrates how a knee implant I is installed onto the distal femur F once the cuts are made.

The blade angle setting for each pass is set according to the shape of the implant surface I1. Because different commercially available implants I have differently shaped implant surfaces I1, the dual-bladed surgical saw allows for the blade angle to be adjusted to match a variety of different implants I. Before the procedure begins, it might be advantageous to prepare a separate template for each commercially available implant I and use the template to indicate the cut lines on the femur F itself prior to making any cuts. The template may also be used to precisely set the blade angle for each pass. Prior to making the cuts, it may be beneficial to superimpose the template of the bone implant to be attached to the bone onto the bone to be cut. This way, the superimposed template can be used as a guide or jig for the surgeon when making the cuts.

Figure 18A:
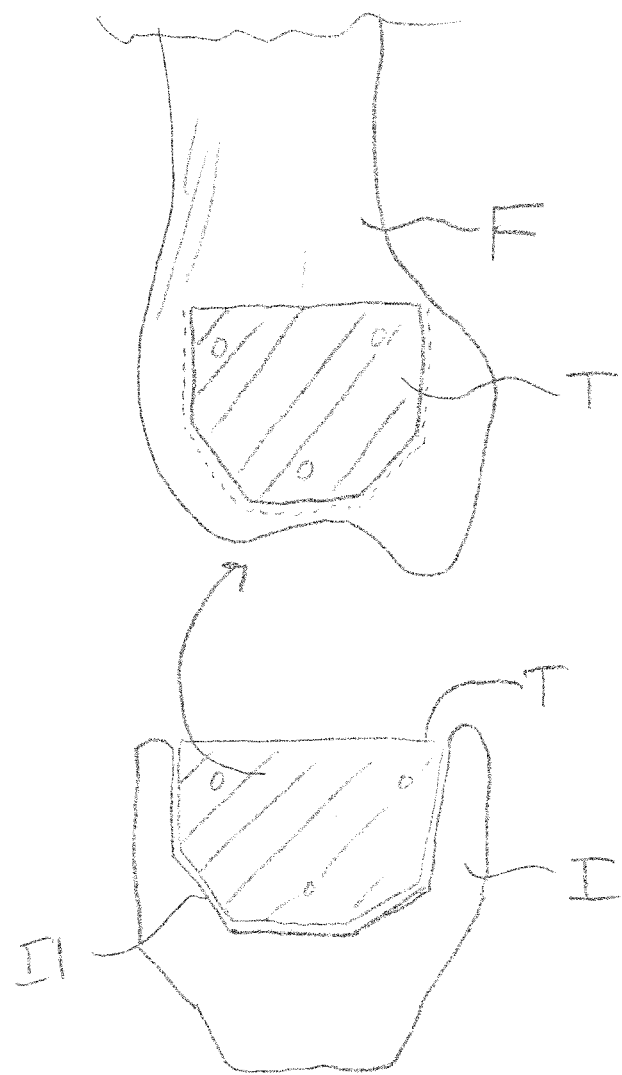
FIGS. 18a and b illustrates the use of a template as a cutting guide.
Figure 18B:
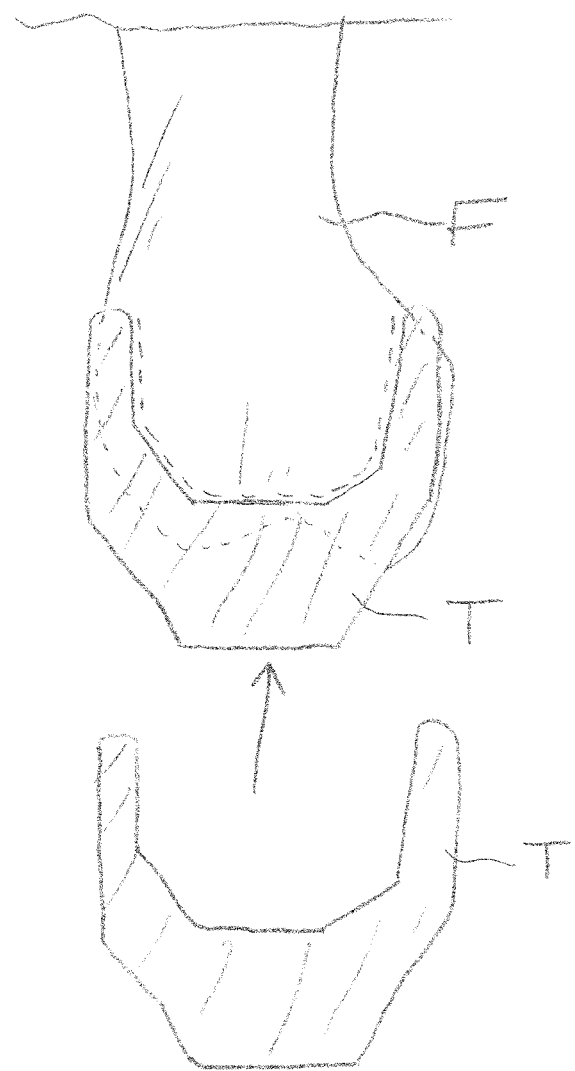

An example of this procedure is illustrated in FIGS. 18a and 18b. In FIG. 18a, a template T is formed using the implant surface I1 as a guide. The template T is then superimposed and temporarily affixed to the femur F in the proper position. The template defines a cutting line (dashed line) on the femur F that substantially matches the shape of the implant surface I1. In this case, the template T may be in the form of a plate, jig, or stencil, depending on its thickness, and the cutting line is defined along it peripheral boundary. If a thicker plate is used, it will act as a jig by keeping the dual saw blades bone cuts in the same plane. If desired, In FIG. 18b, the template T is in the form of a stencil that defines the cutting line along its interior boundary, which matches the shape of the implant surface I1. The surgeon can simply trace the shape of the template T onto the bone prior to cutting.

It should be understood that the actual shape of the template may vary from the two examples depicted here, for example, to better accommodate the multiplanar surface of the side of the femur bone in which the template will be used and/or temporarily affixed thereto.

It should be understood that the method illustrated in FIGS. 16a-d, 17, and 18 is for a particular type of knee implant I. Accordingly, it may be necessary to make more or fewer cuts, depending on the implant surface I1 shape. In any case, however, it will be advantageous to pass the first blade 17 across the previous cut when making a subsequent cut as described.

Referring now to FIG. 19, the method just described may alternatively be performed with a dual-bladed surgical saw 300 having a fixed cutting angle A1 between the blades 17,18. In this example, the cutting angle A1 between blades 17,18 is fixed at an angle that corresponds to an angle between cuts needed to match a particular implant to a bone. The surgeon can use a series of dual-bladed saws fixed to the proper cutting angle A1 if different cutting angles A1 are necessary. In the dual-bladed sagittal-type surgical saw 300 shown in FIG. 19. The blades 17, 18 are affixed to a blade mount shaft 302 such that the proper cutting angle A1 is obtained. In this example, the fixed cutting angle is about 121 degrees, which is, in no way, a limitation to the scope of the invention.

Figure 20:
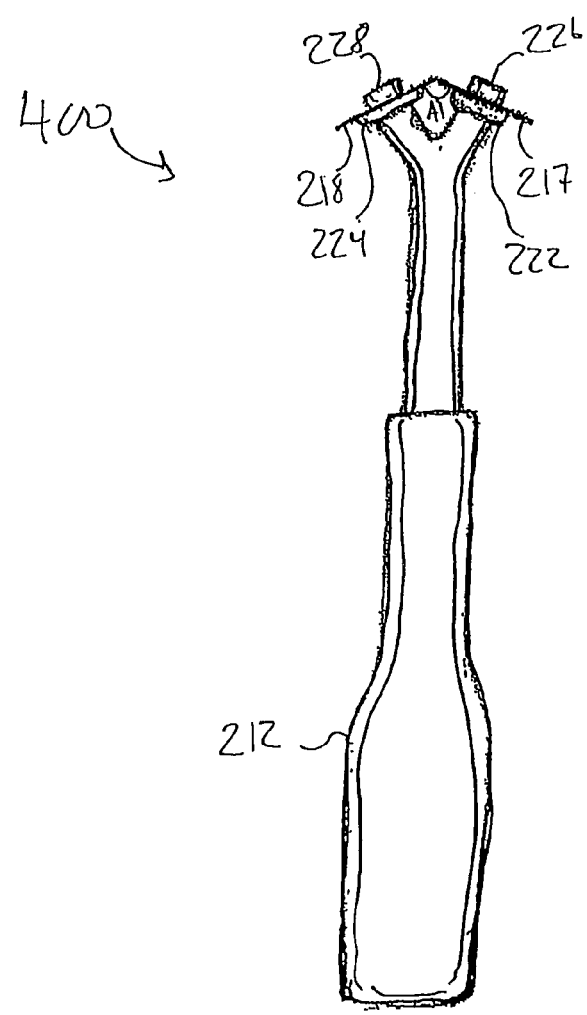
FIG. 20 is a rear isometric view of an oscillator-type dual-bladed surgical saw with a fixed cutting angle, according to a seventh apparatus aspect of the invention.

Referring to FIG. 20, a series of fixed cutting angle oscillator-type dual-bladed surgical saws, such as the saw 400 may also be used to perform the same method. In this example, the saw 400 is essentially the same as the saw 200 shown in FIG. 11, but the cutting angle A1 is about 121 degrees, which is, in no way, a limitation to the scope of the invention.

The invention has been described above with reference to preferred embodiments. Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described. However, the skilled should understand that the methods and materials used and described are examples and may not be the only ones suitable for use in the invention.

The invention has been described in some detail, but it will be apparent that various modifications and changes can be made within the spirit and scope of the invention as described in the foregoing specification and the appended claims.

That which is claimed is:

1. A dual-bladed surgical saw comprising:
    a saw body having a blade assembly attached thereto, the blade assembly being positioned about a rotational axis;
    a first blade radially spaced about the rotational axis, extending outwardly from the blade assembly substantially parallel to the rotational axis, and terminating at a first cutting surface;
    a second blade radially spaced about the rotational axis, extending outwardly from the blade assembly parallel to the rotational axis, and terminating at a second cutting surface;
    an oscillator mechanism coupled to the first and second blades for simultaneously reciprocating the first and second blades;
    wherein the first blade is independently rotatable relative to the second blade about the rotational axis for defining a predetermined cutting angle between the first blade and second blade.

2. The dual-bladed surgical saw of claim 1, wherein the second blade is independently rotatable relative to the first blade about the rotational axis.

3. The dual-bladed surgical saw of claim 1, further comprising an angle adjustment pin extending into the saw body from the blade assembly through the rotational axis, the angle adjustment pin being connected to the first and second blades and including a first position in which the first and second blades are freely rotatable thereabout and a second position in which the first and second blades are fixed in place.

4. The dual-bladed surgical saw of claim 3, wherein the angular adjustment pin includes a threaded section that mates with a threaded bore of a blade assembly mounting member forming part of the saw body and the adjustment pin is movable from the first position to the second position by screwing the threaded section into the threaded bore.

5. The dual-bladed surgical saw of claim 1, wherein the first blade is attached to a distal end of a first blade assembly and the second blade is attached to a distal end of a second blade assembly, the first and second blade assemblies extending outwardly from and non-parallel to the rotational axis so that the distal ends are radially spaced from the rotational axis.

6. The dual-bladed surgical saw of claim 5, further comprising an angle adjustment pin extending into the saw body through the rotational axis and the first and second blade assemblies, the angle adjustment pin including a first position in which the first and second blades are freely rotatable thereabout and a second position in which the first and second blades are fixed in place.

7. The dual-bladed surgical saw of claim 6, wherein the angular adjustment pin includes a threaded section that mates with a threaded bore of a blade assembly mounting member forming part of the saw body and the adjustment pin is movable from the first position to the second position by screwing the threaded section into the threaded bore.

8. The dual-bladed surgical saw of claim 5, wherein the first and second blade assemblies each include an elongated slot passing therethrough and extending towards the respective distal end and further comprising an angle adjustment pin extending into the saw body through the rotational axis and the elongated slots, the angle adjustment pin including a first position in which the first and second blades are freely rotatable and translatable thereabout and a second position in which the first and second blades are fixed in place.

9. The dual-bladed surgical saw of claim 5, wherein the first and second blade assemblies each include an elongated slot passing therethrough and extending towards the respective distal end and further comprising an angle adjustment pin extending into the saw body through the rotational axis and the elongated slots, the first and second blade assemblies being translatable along the elongated slot for changing a radial distance between each blade and the rotational axis.

10. The dual-bladed surgical saw of claim 1, wherein the first blade and second blades are attached to the saw body, respectively, by a first flexible arm and a second flexible arm, the first and second flexible arms being independently movable relative to one another and connected to an arcuate slot defining a path of translation of the first and second blades.

11. A dual-bladed surgical saw comprising:
    a saw body having a first blade assembly and a second blade assembly attached thereto;
    the first blade assembly including a first oscillator for reciprocating a first blade having a cutting surface at an end of the first blade opposite the first oscillator;
    the second blade assembly including a second oscillator for reciprocating a second blade having a cutting surface at an end of the second blade opposite the second oscillator;
    wherein the first blade is independently rotatable relative to the second blade about a rotational axis passing through the first and second blade assemblies for defining a predetermined cutting angle between the first blade and second blade.

12. The dual-bladed surgical saw of claim 11, further comprising first and second blade assembly arms attached, respectively, to the first and second blade assemblies, a goniometer attached to one of the blade assembly arms and a threaded bore in the other blade assembly arm, a goniometer slot passing through the goniometer, and a threaded fastener fitted through the goniometer slot and mated with the threaded bore, the threaded fastener being slidably disposed through the goniometer slot.

13. The dual-bladed surgical saw of claim 11, further comprising an angle adjustment pin extending into the saw body through the first and second blade assemblies through the rotational axis, the angle adjustment pin including a first position in which the first and second blades are freely rotatable thereabout and a second position in which the first and second blades are fixed in place.

14. The dual-bladed surgical saw of claim 13, wherein the angular adjustment pin includes a threaded section that mates with a threaded bore of a blade assembly mounting member forming part of the saw body and the adjustment pin is movable from the first position to the second position by screwing the threaded section into the threaded bore.

15. A method of shaping bone for mating the bone with an implant having an implant surface adapted to abut the shaped bone when installed, the method comprising:
- positioning blades of a dual-bladed surgical saw to a predetermined cutting angle, the dual-bladed surgical saw including
  - a saw body having a blade assembly attached thereto, the blade assembly being positioned about a rotational axis;
  - a first blade radially spaced about the rotational axis, extending outwardly from the blade assembly substantially parallel to the rotational axis, and terminating at a first cutting surface;
  - a second blade radially spaced about the rotational axis, extending outwardly from the blade assembly parallel to the rotational axis, and terminating at a second cutting surface; and
  - an oscillator mechanism coupled to the first and second blades for simultaneously reciprocating the first and second blades;
- simultaneously making first and second adjacent cuts separated by the cutting angle by contacting the bone with the first and second blades while the blades are reciprocating; and
- making a third cut adjacent to the second cut, the third cut being separated from the second cut by the same or a different cutting angle by passing the first blade across the second cut while the second blade makes the third cut.

16. The method of claim 15, further comprising adjusting the cutting angle between subsequent cuts by rotating at least one of the blades about the rotational axis.

17. The method of claim 15, further comprising adjusting the cutting angle between subsequent cuts by rotating at least one of the blades about the rotational axis to a position at which planes defined by the first and second blades are parallel to planes defined by a pair of implant surfaces adapted to abut the bone when installed thereon.

18. The method of claim 15, further comprising, prior to making the first and second cuts, superimposing a template of a bone implant to be attached to the bone onto the bone to be cut, wherein the first, second and third cuts are made using the superimposed template as a guide.

19. The method of claim 15, wherein the first blade is independently rotatable relative to the second blade about the rotational axis for defining the predetermined cutting angle between the first blade and second blade.

20. The method of claim 15, wherein the dual-bladed surgical saw further includes an angle adjustment pin extending into the saw body from the blade assembly through the rotational axis, the angle adjustment pin being connected to the first and second blades and including a first position in which the first and second blades are freely rotatable thereabout and a second position in which the first and second blades are fixed in place.

* * * * *